United States Patent
Ischinger

(10) Patent No.: US 9,937,333 B2
(45) Date of Patent: Apr. 10, 2018

(54) BALLOON CATHETER FOR TREATMENT OF A VESSEL AT A BIFURCATION

(71) Applicant: Thomas Ischinger, Munich (DE)

(72) Inventor: Thomas Ischinger, Munich (DE)

( * ) Notice: Subject to any disclaimer, the term of this patent is extended or adjusted under 35 U.S.C. 154(b) by 169 days.

(21) Appl. No.: 14/841,835

(22) Filed: Sep. 1, 2015

(65) Prior Publication Data

US 2017/0056626 A1    Mar. 2, 2017

(51) Int. Cl.
*A61M 25/10* (2013.01)
*A61F 2/958* (2013.01)
*A61F 2/954* (2013.01)

(52) U.S. Cl.
CPC .......... *A61M 25/104* (2013.01); *A61F 2/954* (2013.01); *A61F 2/958* (2013.01); *A61M 25/1002* (2013.01); *A61M 2025/1045* (2013.01); *A61M 2025/1079* (2013.01)

(58) Field of Classification Search
CPC ........... A61F 2/958; A61M 2025/1045; A61M 2025/1079; A61M 25/1002; A61M 25/104
See application file for complete search history.

(56) References Cited

U.S. PATENT DOCUMENTS

| 5,219,355 | A | * | 6/1993 | Parodi | A61F 2/07 604/101.01 |
|---|---|---|---|---|---|
| 5,520,647 | A | | 5/1996 | Solar | |
| 5,569,199 | A | | 10/1996 | Solar | |
| 5,662,608 | A | * | 9/1997 | Imran | A61M 25/1002 604/103.07 |
| 5,893,887 | A | | 4/1999 | Jayaraman | |
| 6,165,195 | A | * | 12/2000 | Wilson | A61F 2/856 606/108 |
| 6,475,226 | B1 | * | 11/2002 | Belef | A61B 1/3137 606/170 |
| 6,491,719 | B1 | | 12/2002 | Fogarty et al. | |
| 6,682,556 | B1 | | 1/2004 | Ischinger | |
| 2001/0016767 | A1 | | 8/2001 | Wilson et al. | |
| 2003/0050688 | A1 | | 3/2003 | Fischell et al. | |
| 2003/0187494 | A1 | | 10/2003 | Loaldi | |
| 2004/0186560 | A1 | * | 9/2004 | Alt | A61F 2/91 623/1.35 |
| 2005/0113686 | A1 | | 5/2005 | Peckham | |
| 2005/0154447 | A1 | | 7/2005 | Goshgarian | |
| 2005/0222672 | A1 | | 10/2005 | Shmulevitz | |
| 2005/0245941 | A1 | * | 11/2005 | Vardi | A61F 2/954 606/108 |

(Continued)

FOREIGN PATENT DOCUMENTS

| WO | 2000057813 | 5/2000 |
|---|---|---|
| WO | 2009140719 | 11/2009 |
| WO | 2012062144 | 5/2012 |

*Primary Examiner* — Julie A Szpira
(74) *Attorney, Agent, or Firm* — AlphaPatent Associates, Ltd; Daniel J. Swirsky

(57) ABSTRACT

A balloon catheter having a balloon with a shape for treating a vessel at a bifurcation, includes an oblique proximal end of the balloon, and a catheter shaft which is at least partially eccentric to a central axis of the balloon. Markers used for longitudinal and rotational alignment are included on the catheter shaft. A torque transmission element may be used for transmitting torque from the stiff proximal segment of the catheter to the distal flexible balloon segment of the catheter.

20 Claims, 14 Drawing Sheets

(56) References Cited

U.S. PATENT DOCUMENTS

| | | | |
|---|---|---|---|
| 2006/0064064 A1* | 3/2006 | Jang | A61M 25/1002 |
| | | | 604/194 |
| 2006/0106448 A1* | 5/2006 | Shaked | A61B 17/12022 |
| | | | 623/1.11 |
| 2007/0021685 A1* | 1/2007 | Oepen | A61M 25/09 |
| | | | 600/585 |
| 2007/0021816 A1 | 1/2007 | Rudin | |
| 2007/0118200 A1* | 5/2007 | Weber | A61F 2/954 |
| | | | 623/1.11 |
| 2009/0091066 A1 | 4/2009 | Sleva et al. | |
| 2009/0171426 A1 | 7/2009 | Magnuson | |
| 2010/0070014 A1 | 3/2010 | Viller | |
| 2012/0191173 A1 | 7/2012 | Gunderson et al. | |
| 2014/0277377 A1 | 9/2014 | Ischinger | |
| 2015/0112256 A1* | 4/2015 | Byrne | A61M 25/10 |
| | | | 604/103.02 |

* cited by examiner

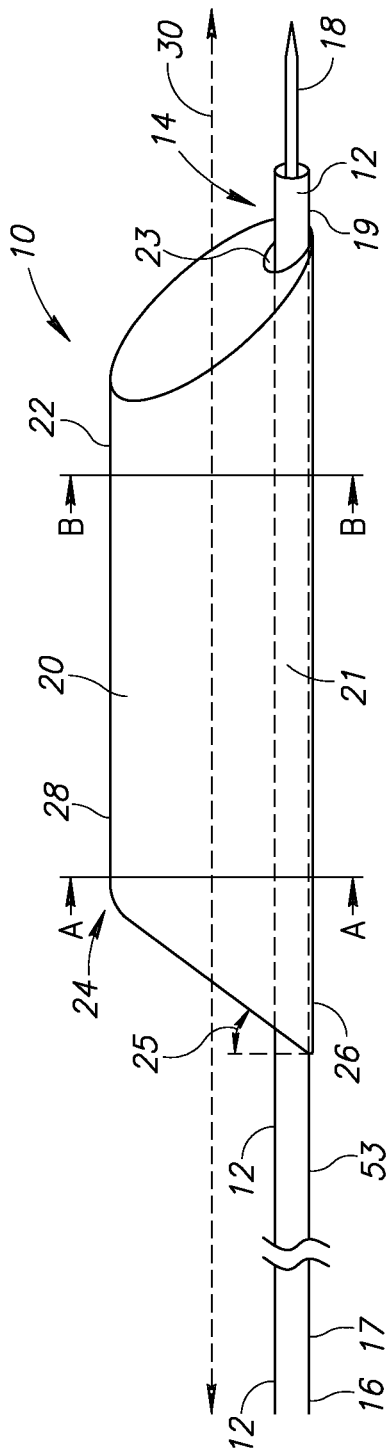
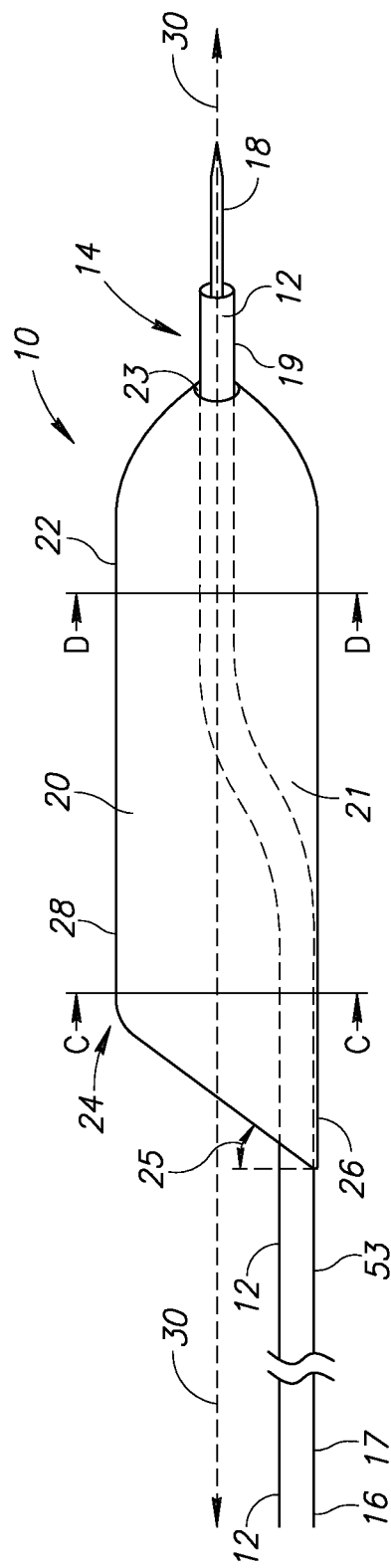
FIG.1A
FIG.1B

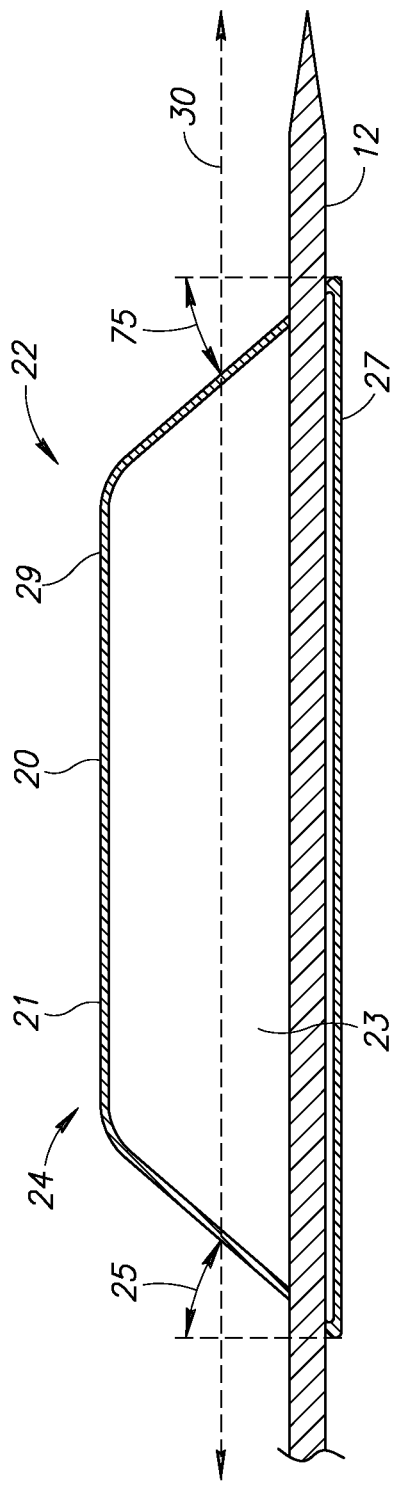
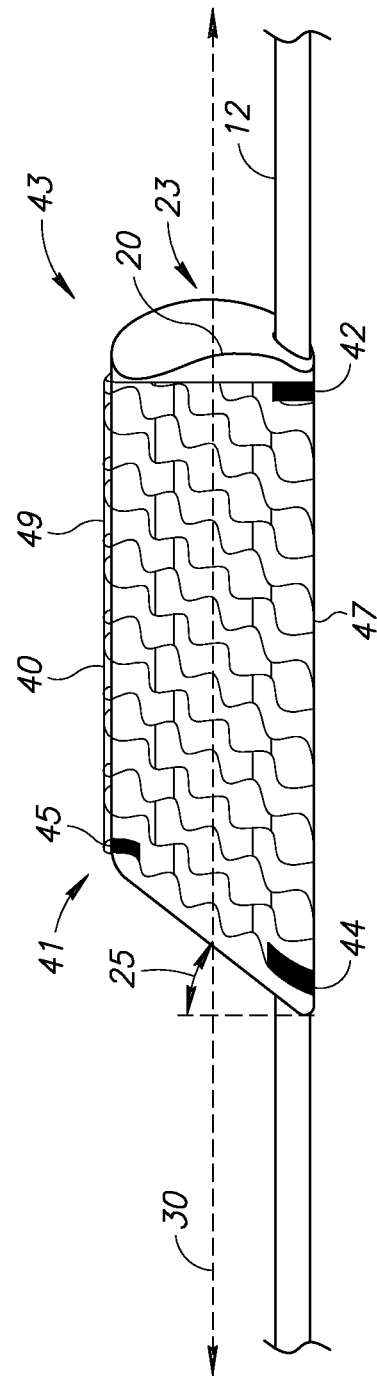
FIG.4
FIG.5

BALLOON CATHETER FOR TREATMENT OF A VESSEL AT A BIFURCATION

TECHNICAL FIELD

The invention is directed to a balloon catheter for use in treating a vessel at a bifurcation.

BACKGROUND

A lesion located at or near a bifurcation in a vessel, such as at the ostium of a side branch which extends from a main branch or in the main branch at a bifurcation, may be treated using a balloon catheter or a catheter with a stent. However, treatment of such lesions is a challenge. If a balloon is used to treat an ostial lesion of a side branch, the atherosclerotic plaque may be displaced by the balloon dilatation or by stent or scaffold implantation towards the main branch, thereby creating a new obstruction by "plaque shift." In particular this complication is likely to occur when the lesion is located at the carina, that is, the distal branchpoint of the two vessels forming the bifurcation.

In order to avoid this complication, a technique known as the "kissing balloon" technique is often used, wherein simultaneous dilatation of the main branch and the side branch is performed. In this technique, two balloons are introduced separately into each of the vessel and are simultaneously inflated. However, this results in two inflated balloons lying parallel to each other in the main branch, creating a non-circular dilatation body in the main branch, potentially resulting in vessel trauma and non-homogenously distributed dilatation forces upon the vessel wall. Moreover, if a stent or scaffold has already been placed in the main branch, the kissing balloon technique with two balloons lying over a particular length parallel to each other within the stent or scaffold results in distortion of the stent or scaffold due to the non-circular dilatation body and partial separation of the stent from the vessel wall. This is known to carry the risk of early and late complications such as vessel thrombosis, restenosis or occlusion and interruption of homogenous drug elution from the stent to the vessel wall in the case of drug eluting stents.

Similarly, when a stent or stents or scaffolds are used, overlapping of stents or protrusion of a stent from the ostium of a side branch into the main branch may also result in vessel trauma or unwanted plaque shifts, or may result in flow obstruction, thrombosis formation, and potentially distortion or crushing of stent materials if a balloon dilatation in the main branch is performed or if a second stent is later introduced in the main branch bridging the side branch ostium.

U.S. patent application Ser. No. 13/826,399 to Ischinger, which has been published as US Patent Publication Number 2014/0277,377A1, discloses an oblique stent which is designed to more closely fit the bifurcation anatomy, thus minimizing the protrusion of a portion of the stent material from the side branch into the main branch or vice versa. With the use of an oblique shaped stent, less metal protrusion and distortion occurs, but the problems of plaque shift and/or main vessel compromise may still exist.

U.S. Pat. No. 6,682,556 to Ischinger discloses a balloon catheter for more precise placement of an oblique stent into a side branch. However, the balloon catheter disclosed therein includes a conventional angioplasty balloon, which in its inflated state has a body section and further includes a proximal section and a distal section, both of which exhibit a symmetrical cone shape. The cone shape of the two end-sections includes the balloon tip, and symmetrical balloon shoulders which merge into the balloon body.

Thus, a balloon specifically shaped to better match the bifurcational anatomy and/or the shape of an oblique stent or scaffold would result in more successful bifurcation treatment, including less traumatic and less harmful kissing balloon techniques.

There is thus a need for a torquable balloon which better suits the bifurcational anatomy and permits conventional stent or scaffold and oblique stent or oblique scaffold deployment in a side branch ostium or in a diseased vessel bifurcation and further provides balloon dilatation of an ostial lesion or a vessel bifurcation, without obstructing flow in the main branch or leading to stent or scaffold material distortion and permitting kissing balloon techniques minimizing their current risks.

SUMMARY

There is provided, in accordance with embodiments of the invention, a balloon catheter having a shaft, wherein the shaft has a shaft distal end and a shaft proximal end along a longitudinal axis, and a balloon positioned on the shaft, wherein the balloon has a balloon distal end and a balloon proximal end along the longitudinal axis, wherein the balloon proximal end has a long wall portion and a short wall portion opposite the long wall portion wherein the long wall portion extends past the short wall portion in a proximal direction along the longitudinal axis, such that the balloon proximal end is substantially at an oblique angle to a plane which is perpendicular to the longitudinal axis when the balloon is in an expanded state. Thus, in embodiments of the invention, the balloon proximal end, and optionally also the balloon distal end, exhibit an asymmetrical shape.

In accordance with further features in embodiments of the invention, the shaft may be a guidewire shaft having a guidewire lumen configured to hold a guidewire therein. In accordance with embodiments of the invention, the shaft may be at least partially comprised of a relatively stiff segment, such as a hypotube, and may be comprised of a metal such as stainless steel, titanium, nitinol, or any other suitable relatively stiff material. In some embodiments, the hypotube is partially slit (for example, by laser cutting), in order to increase longitudinal flexibility while maintaining rotational stability (i.e. torquability). The shaft may include a more flexible distal portion to provide ease of movement through the tortuous blood vessels, and the flexible distal portion may include the balloon segment. In some embodiments, a transition area between the distal (balloon) segment and the proximal, stiff segment (i.e. hypotube) may be comprised of a polymer tubing, and may further include a braiding or mesh element or a spiral wire element or a fixed or movable torque reinforcing external sheath to increase torque transmission from the proximal end of the shaft to the distal end.

In accordance with further features in embodiments of the invention, the guidewire may be freely movable through the shaft, or it may be integrated with the shaft, or alternatively the guidewire may be fixed at the distal end of the shaft (i.e. fixed wire system). In some embodiments, the guidewire shaft may extend through the entire length of the catheter (i.e. over the wire system), and in other embodiments, the guidewire shaft may extend from the distal end of the catheter to an exit point along the length of the catheter (i.e. rapid exchange system). In some embodiments, a combination of over the wire and rapid exchange may be used, wherein a guidewire lumen extends through the entire length of the catheter, but at least one exit port is positioned between the distal and proximal ends of the catheter.

In accordance with further embodiments, the shaft may be positioned through the balloon and adjacent to the long wall portion at the balloon proximal end such that at the balloon proximal end, the shaft is eccentric to a central axis of the balloon when the balloon is in a deployed (i.e. expanded) state. In accordance with further embodiments, at the distal end of the balloon, the shaft is positioned substantially at the central axis of the balloon, such that when the balloon is in a deployed state, the shaft is partially eccentric to the central axis of the balloon and partly concentric to the central axis of the balloon. In some embodiments, the shaft is angled within the body of the balloon.

In accordance with further features in embodiments of the invention, the balloon catheter may include markers for visualization of the catheter. The markers disclosed herein may be radiopaque, or may be comprised of another type of material imaging with different modalities other than x-ray. The markers include a first proximal marker on the shaft at the proximal end of the long wall portion, and a second proximal marker on the shaft at the proximal end of the short wall portion. To allow for visualization with x-ray imaging or other imaging modalities of rotational positioning of the catheter, the first proximal marker may have a triangular shape having an angle approximating the oblique angle of the balloon end, or may have a tilted ring configuration or another suitable configuration. The first and second proximal markers may be arranged on the shaft in positions by which the the radiographically visible elements are eccentric (opposite) to each other so that rotational position of shaft or balloon can be visualized by imaging. Alternatively, the markers may be applied to the balloon or incorporated within the balloon material instead of or in addition to being positioned on the shaft.

In embodiments of the invention, the balloon catheter may further include an oblique stent or scaffold positioned on the balloon, wherein a proximal end of the oblique stent is configured at an oblique angle to the plane which is perpendicular to the longitudinal axis of the shaft. In some embodiments, the oblique angle of the balloon end and the oblique angle of the stent end are approximately the same. The term "stent" used herein includes all variations of stents, scaffolds, and stent grafts used for treating vessels or other luminal organs, including conventional bare metal or drug eluting stents, for example, and also including any material suitable for use in a stent, stent graft or scaffold, for example, metals, textiles, polymers, permanent or bioabsorbable materials, balloon-expandable or self-expandable or hybrid materials.

In accordance with further features of the invention, in some embodiments a diameter of the balloon proximal end is greater than a diameter of the balloon distal end when the balloon is in an expanded state. In some embodiments, the balloon distal end has a distal long wall portion and a distal short wall portion opposite the distal long wall portion wherein the distal long wall portion extends past the distal short wall portion in a distal direction along the longitudinal axis such that the balloon distal end is also at an oblique angle to a plane which is perpendicular to the longitudinal axis when the balloon is in an expanded state.

In accordance with further features in embodiments of the invention, the balloon catheter may further include a torque transmission mechanism to transmit rotational torque from the proximal end of the shaft to the balloon by increasing friction between the guidewire and the guidewire shaft. This mechanism may be a key lock mechanism or other torque transmission mechanism, as will be described in greater detail.

There is provided, in accordance with embodiments of the invention, a balloon catheter having a shaft with a shaft distal end and a shaft proximal end along a longitudinal axis, and a balloon positioned on the shaft, the balloon having a balloon first end and a balloon second end along the longitudinal axis, wherein at the balloon first end, the shaft is positioned through the balloon and adjacent to an edge of the balloon and wherein at the second balloon end, the shaft is positioned substantially at the central axis of the balloon, such that at the balloon first end, the shaft is eccentric to a central axis of the balloon and at the balloon second end the shaft is substantially concentric to the central axis of the balloon when the balloon is in an expanded state. In some embodiments, the balloon first end is the balloon proximal end and the balloon second end is the balloon distal end. In some embodiments, the balloon is a conventional balloon shape. In other embodiments, the balloon proximal end has a long wall portion and a short wall portion opposite the long wall portion wherein the long wall portion extends past the short wall portion in a proximal direction along the longitudinal axis, such that the balloon proximal end is substantially at an oblique angle to a plane which is perpendicular to the longitudinal axis when the balloon is in an expanded state.

There is provided, in accordance with embodiments of the invention, a method of treating a vessel at a bifurcation. The method includes introducing a first balloon catheter into the vessel (for example, the side branch), the first balloon catheter including a first balloon having a long wall portion and a short wall portion at a proximal end thereof, positioning the first balloon catheter such that the long wall portion is at the proximal branchpoint of the side branch, while not protruding into the main branch, and the short wall portion is at the carina (i.e. the distal branchpoint of the side branch), and expanding the first balloon within the vessel. In some embodiments, a second balloon catheter having a second balloon with a second balloon long wall portion and a second balloon short wall portion is introduced into the main vessel and positioned such that the first balloon catheter is extended into a first branch vessel and the second balloon catheter is extended from the main branch into a second branch vessel, and wherein the second balloon is expanded within the vessel, such that when the first balloon and second balloon are inflated simultaneously, they are in a kissing position without a significant area in the main branch having parallel balloons therein. In other embodiments, a second balloon catheter having a conventionally shaped balloon is introduced into the main vessel such that the second balloon catheter crosses the carina and bridges the first branch vessel. The conventionally shaped balloon may then be expanded within the vessel, either simultaneously or non-simultaneously with the first balloon. In other embodiments, a first oblique stent is positioned on the first balloon and is deployed in the branch vessel such that a long portion of the oblique stent is at the branch point which is most proximal to the main branch and a short portion of the oblique stent is at the carina of the bifurcation, such that substantially no protrusion of stent material into the main branch occurs. In some embodiments, a balloon is inflated in the main branch bridging the side branch simultaneously with inflation of the stent deploying balloon so that the carina is protected without metal or other material crush or balloon trauma in the main branch. In yet additional embodiments, two oblique balloons or two oblique balloons with stents for deployment in each of the two branch vessels are deployed simultaneously.

Unless otherwise defined, all technical and scientific terms used herein have the same meaning as commonly understood by one of ordinary skill in the art to which this invention belongs. Although methods and materials similar or equivalent to those described herein can be used in the practice or testing of the embodiments of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of various embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several embodiments of the invention may be embodied in practice.

In the drawings:

FIGS. 1A and 1B are schematic illustrations of a balloon catheter in accordance with embodiments of the invention;

FIG. 4 is a longitudinal cross-sectional illustration of a balloon having oblique ends at its proximal and distal ends, in accordance with embodiments of the invention;

FIG. 5 is an illustration of the balloon catheter of FIG. 1A or 1B, further including an oblique stent or scaffold positioned on the balloon, in accordance with embodiments of the invention;

Figure 2A:
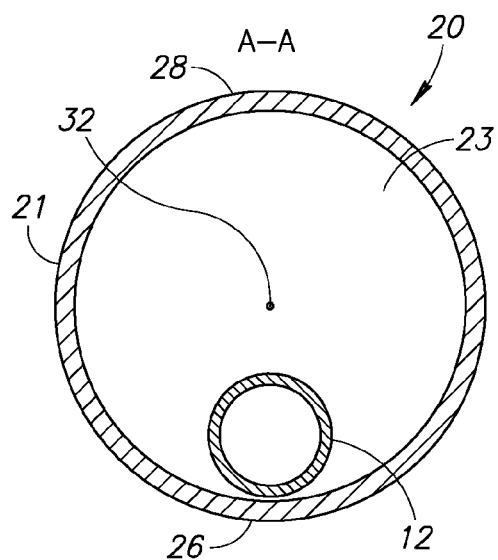
FIGS. 2A-2B are cross-sectional illustrations of the catheter of FIG. 1A.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the invention. It will be understood by those of ordinary skill in the art that embodiments of the invention may be practiced without these specific details. In other instances, well-known methods, procedures, components and structures may not have been described in detail so as not to obscure the invention.

The invention relates to a balloon catheter for treatment of a lesion at a bifurcation. Further advantages of the design of the balloon catheter of the invention will be described herein below.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Reference is now made to FIGS. 1A and 1B, which are schematic illustrations of a balloon catheter 10 in accordance with embodiments of the invention. Catheter 10 includes a shaft 12 having a shaft distal end 14 and a shaft proximal end 16 along a longitudinal axis 30. In some embodiments, shaft 12 is a guidewire shaft having a guidewire lumen suitable for holding a guidewire 18 therein. Guidewire lumen may extend along a length of shaft 12 from shaft distal end 14 to shaft proximal end 16 for an "over the wire" configuration. Alternatively, a guidewire exit point may be positioned at a point along shaft 12 for a "rapid exchange" configuration. In alternative embodiments, shaft 12 does not include a guidewire lumen and instead, a fixed wire is attached to shaft 12, for example at shaft distal end 14.

An expandable balloon 20 is positioned on shaft 12. In some embodiments, balloon 20 is positioned at or near shaft distal end 14. Shaft 12 may include a stiff segment 17, extending from a point proximal to balloon 20 to shaft proximal end 16, and a flexible segment 19 having balloon 20 positioned thereon. Stiff segment 17 may be comprised of a hypotube or a relatively stiff wire or any other material which has enough stiffness to transmit torque forces from one end to the other. Flexible segment 19 is comprised of a substantially flexible material, such as a soft polymer or any material which can bend sufficiently to account for twist and turns within the vessel. Balloon 20 is positioned on flexible segment 19. The stiffness of shaft 12 may decrease over a transition segment 53, which may be for example, an extended portion of shaft 12 wherein the decrease in stiffness occurs gradually or may be a point along shaft 12 wherein the decrease in stiffness occurs abruptly with change of material. Balloon 20 may be an inflatable balloon, or may be expandable by other means, such as via removal of a sheath, for example. Balloon 20 may be substantially tubular and has a balloon distal end 22 and a balloon proximal end 24 along longitudinal axis 30. Balloon 20 includes a balloon wall 21 enclosing a balloon inner space 23. Balloon inner space 23 may be filled with an inflation fluid, as is known in the art, to inflate balloon 20. At balloon proximal end 24, balloon wall 21 includes a long wall portion 26 and a short wall portion 28, wherein long wall portion 26 extends past short wall portion 28 in a proximal direction such that balloon proximal end 24 is substantially at an oblique angle to a plane which is perpendicular to longitudinal axis 30 when balloon 20 is in an inflated state. The oblique angle is shown schematically in FIG. 1A by arrows 25. The oblique angle may be any angle in a range of less than 90 degrees, and in embodiments of the invention may be in a range of between 30 degrees and 70 degrees, for example. A balloon having an oblique angle at a proximal end thereof provides certain advantages over current balloon designs, particularly as relates to anatomy of bifurcations. For example, the use of a balloon having an oblique angle at a proximal end thereof in accordance with embodiments of the invention allows for a kissing balloon technique wherein two balloons can meet at a point of bifurcation without substantial displacement of plaque or other complications associated with the use of two round shaped balloons positioned side by side in a main branch. In addition, the use of a balloon having an oblique angle at a proximal end thereof in accordance with embodiments of the invention provides a platform for delivery of an oblique stent, such as ones disclosed in U.S. patent application Ser. No. 13/826,399, which has been published as US Patent Publication Number 2014/0277,377A1, incorporated by reference herein in its entirety.

Figure 2B:
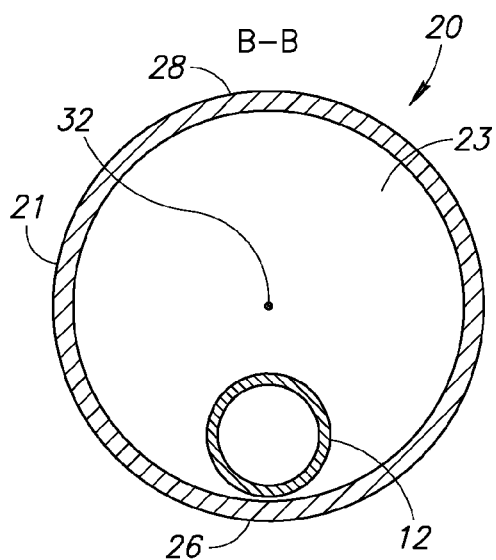
Figure 3A:
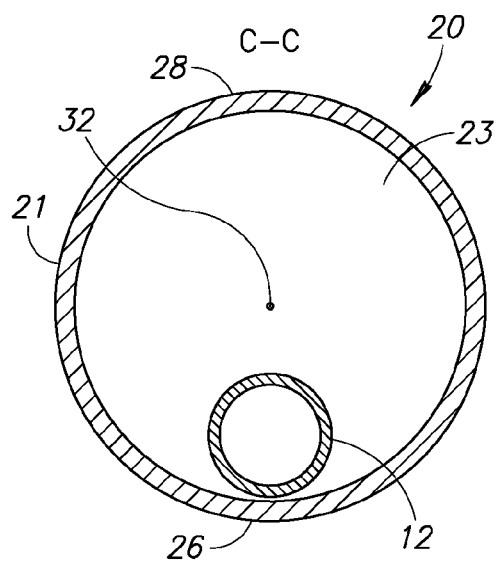
FIGS. 3A and 3B are cross-sectional illustrations of the catheter of FIG. 1B.
Figure 3B:
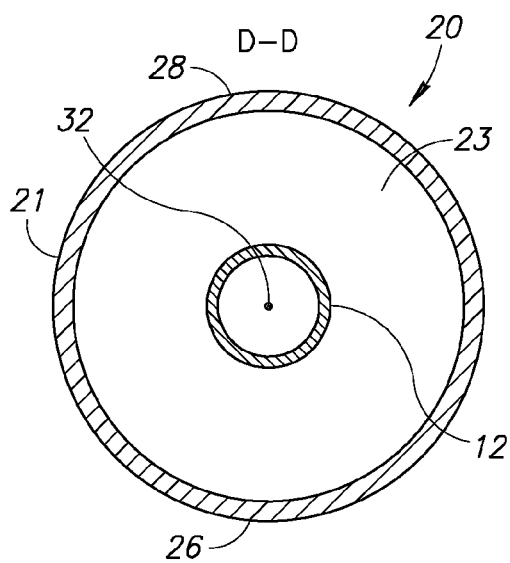

Reference is now made to FIGS. 2A-2B, which are cross-sectional illustrations of catheter 10 of FIG. 1A, and to FIGS. 3A and 3B, which are cross-sectional illustrations of catheter 10 of FIG. 1B. Balloon 20 has a central axis 32 at a center of a cross section of balloon 20. In some embodiments, as shown in FIG. 1A and corresponding FIGS. 2A and 2B, shaft 12 is positioned adjacent to long wall portion 26 of balloon 20 along the length of balloon 20. In this way, shaft 12 is eccentric to central axis 32 along the entire length of balloon 20. Shaft 12 is shown eccentric to central axis 32 at balloon proximal end 24 along lines A-A in FIG. 2A. Shaft 12 is shown eccentric to central axis 32 at balloon distal end 22 along lines B-B in FIG. 2B. In other embodiments, as shown in FIG. 1B and corresponding FIGS. 3A and 3B, shaft 12 is positioned adjacent to long wall portion 26 of balloon 20 at balloon proximal end 24, such that at balloon proximal end 24, shaft 12 is eccentric to central axis 32. However, at balloon distal end 22, shaft 12 is concentric to central axis 32. This can be accomplished, for example, by angling shaft 12 within inner space 23 of balloon 20. Shaft 12 is shown eccentric to central axis 32 at balloon proximal end 24 along lines C-C in FIG. 3A. Shaft 12 is shown concentric to central axis 32 at balloon distal end 22 along lines D-D in FIG. 3B.

Reference is now made to FIG. 4, which is a cross-sectional illustration of balloon 20 shown along longitudinal axis 30, wherein both balloon proximal end 24 and balloon distal end 22 are at oblique angles to a plane which is perpendicular to longitudinal axis 30. In this embodiment, at balloon distal end 22, balloon wall 21 includes a distal long wall portion 27 and a distal short wall portion 29, wherein distal long wall portion 27 extends past distal short wall portion 29 in a distal direction such that balloon distal end 22 is substantially at an oblique angle to a plane which is perpendicular to longitudinal axis 30 when balloon 20 is in an inflated state. The distal oblique angle is shown schematically in FIG. 4 by arrows 75. The distal oblique angle may be the same or may be different than the angle at the proximal end, depicted by arrows 25.

Reference is now made to FIG. 5, which is an illustration of balloon catheter 10 having an oblique stent or scaffold 40 positioned on balloon 20. Oblique stent or scaffold 40 has a stent proximal end 41 and a stent distal end 43. A shape of oblique stent 40 approximates a shape of balloon 20, wherein stent proximal end 41 is at an oblique angle to a plane which is perpendicular to longitudinal axis 30, as shown by arrows 25. Markers may be included on oblique stent 40, as will be described further hereinbelow.

Figure 6A:
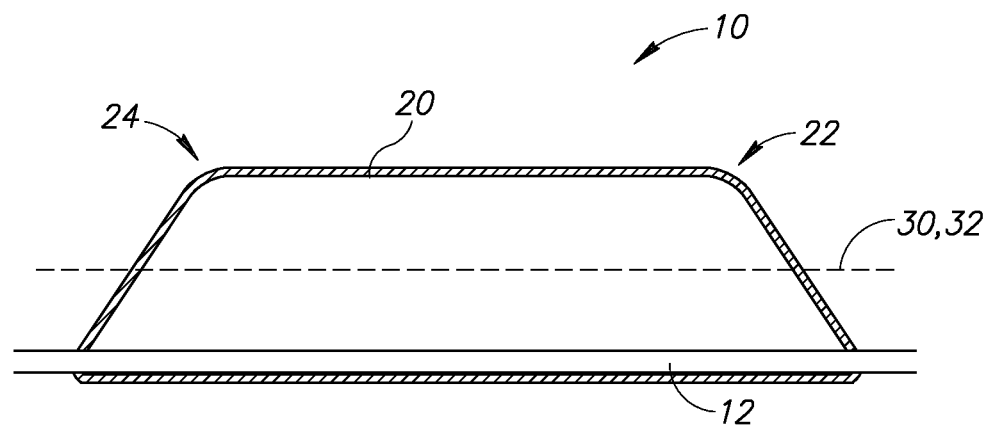
FIGS. 6A-6C are longitudinal cross-sectional illustrations of a balloon catheter, in accordance with embodiments of the invention.
Figure 6B:
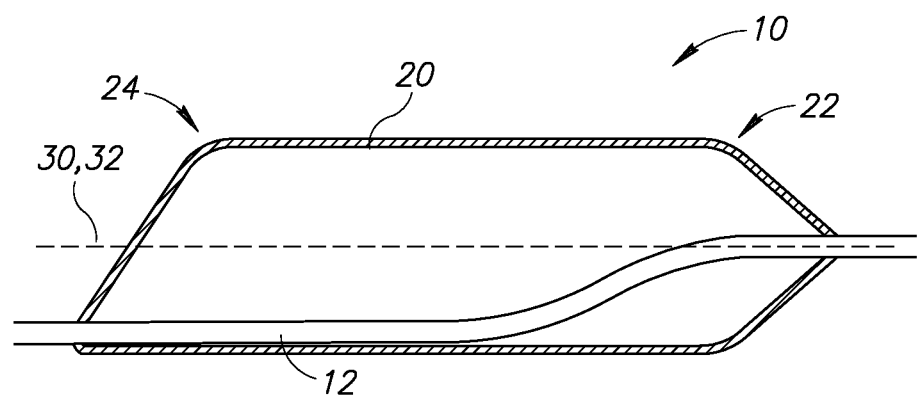
Figure 6C:
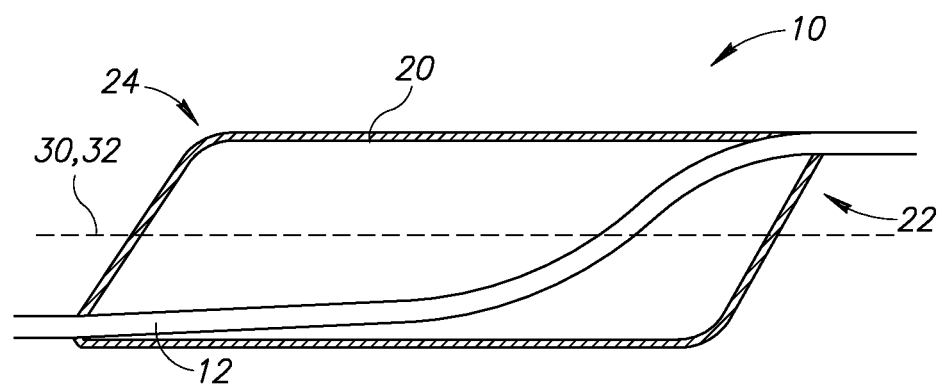

Reference is now made to FIGS. 6A-6C, which are schematic illustrations showing the relationships between balloon 20 and shaft 12, in accordance with embodiments of the invention. As shown in FIG. 6A, in one embodiment, balloon 20 has two oblique ends, wherein balloon proximal end 24 is oblique having an angle in one direction and balloon distal end 22 is oblique having an angle in an opposite direction. Shaft 12 has a straight configuration, and runs along the long wall portions of balloon proximal end 24 and balloon distal end 22, such that shaft 12 is eccentric to central axis 32 of balloon 20 at both balloon proximal end 24 and balloon distal end 22. Central axis 32 runs along longitudinal axis 30 at a center point of balloon 20. As shown in FIG. 6B, in another embodiment, balloon proximal end 24 is oblique, and balloon distal end 22 is symmetric, as in conventional balloon designs. In this embodiment, shaft 12 has an angled configuration, such that shaft 12 runs along the long wall portion of balloon proximal end 24 and exits substantially at a point concentric to central axis 32 of balloon 20. As shown in FIG. 6C, in yet another embodiment, balloon proximal end 24 is oblique and balloon distal end 22 is oblique having an angle that is in substantially the same direction as the angle of balloon proximal end 24, thus forming an approximate parallelogram shape. In this embodiment, shaft 12 is eccentric to central axis 32 at balloon proximal end 24 and is also eccentric to central axis 32 at balloon distal end but is at on an opposite side of central axis 32. Shaft 12 has an angled configuration so that it can extend from one end of central axis 32 at balloon proximal end 24 and through an approximately opposite end of central axis 32 at balloon distal end 22.

Figure 7A:
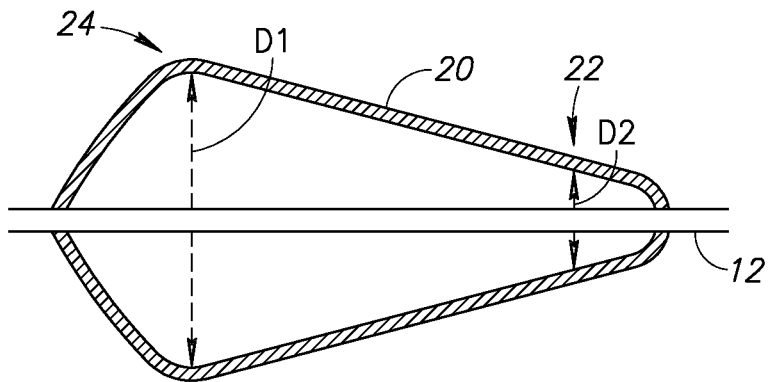
FIGS. 7A-7D are longitudinal cross-sectional illustrations of a balloon in accordance with embodiments of the invention, wherein a diameter of the balloon is larger at the balloon proximal end than at the balloon distal end.
Figure 7B:
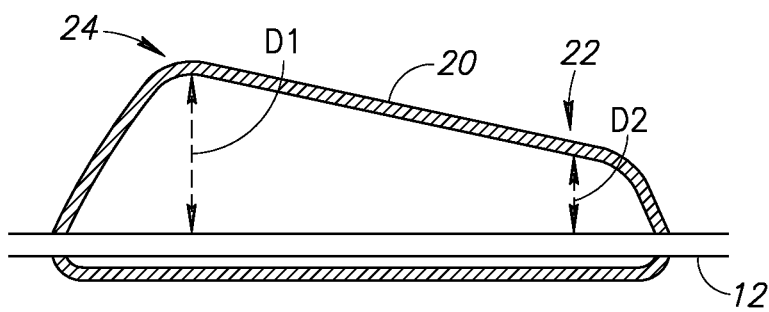
Figure 7C:
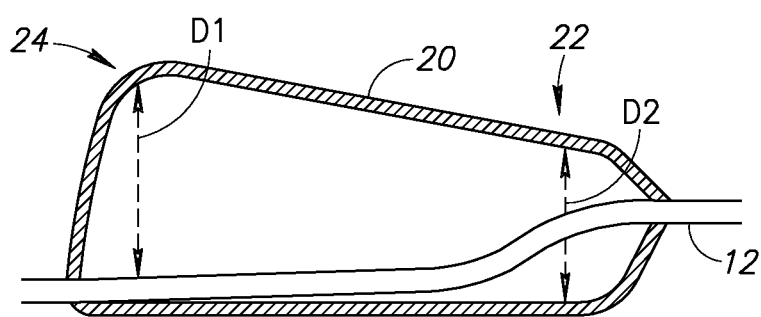
Figure 7D:
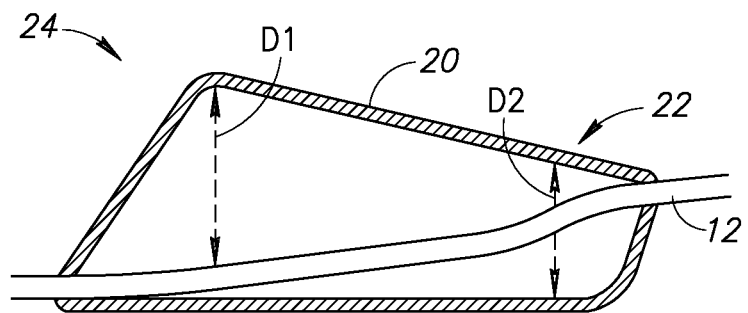

In some embodiments, as shown in FIGS. 7A-7D in longitudinal cross-section, a diameter (D1) of balloon 20 is larger at balloon proximal end 24 than a diameter (D2) at balloon distal end 22. The difference in diameter (D1−D2) between balloon proximal end 24 and balloon distal end 22 may be in a range of, but is not limited to, 0.25-1.5 mm, for example. For example, a diameter D1 of balloon 20 at balloon proximal end 24 may be in a range of 3.25 mm-3.5 mm, while a diameter D2 of balloon 20 at balloon distal end 22 may be in a range of 2.75 mm-3.0 mm. Alternatively, a diameter D1 of balloon 20 at balloon proximal end 24 may be in a range of 3.0-3.25, while a diameter D2 of balloon 20 at balloon proximal end 24 may be in a range of 2.25-2.75. These examples are merely for illustrative purposes, and any difference in balloon diameter between balloon proximal end 24 and balloon 22 is included within the scope of the invention. In FIG. 7A, an example is shown wherein balloon 20 has a conventional shape (i.e. no oblique ends), and wherein D1 is greater than D2. Additional examples are shown in FIGS. 7B, 7C and 7D, corresponding to the descriptions of balloon 20 in FIGS. 6A, 6B and 6C, but wherein a diameter D1 of balloon proximal end 24 is greater than a diameter D2 of balloon distal end 22.

Figure 8A:
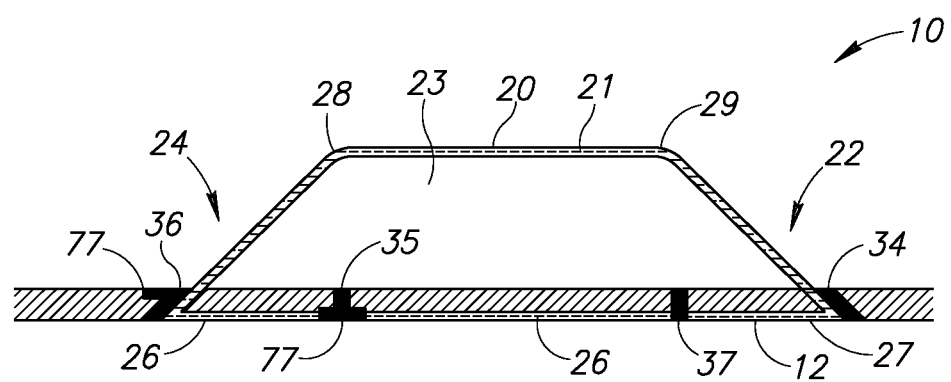
FIGS. 8A-8C are cross-sectional illustrations showing the balloon catheter of FIGS. 1A and 1B with markers for visualization of the balloon catheter within a vessel.
Figure 8B:
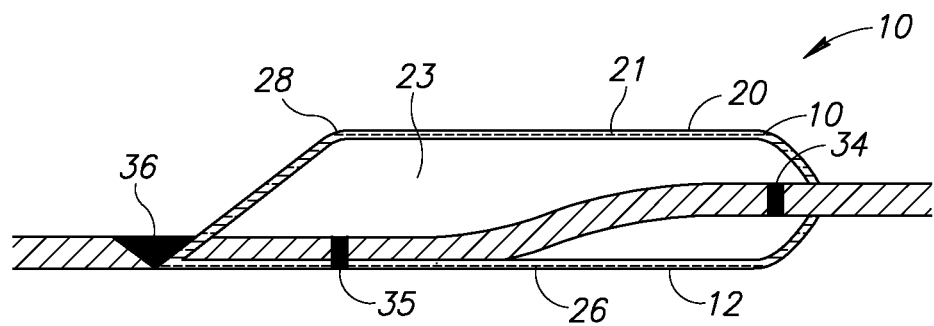
Figure 8C:
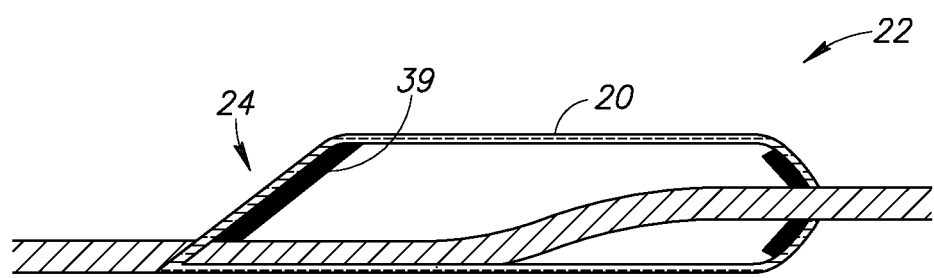

Reference is now made to FIGS. 8A-8C, which are cross-sectional illustrations showing balloon catheter 10 with markers on shaft 12 or on balloon 20 for visualization of catheter 10 within the vessel. Markers may be radiopaque markers or may be comprised of other materials used for other imaging modalities. The use of markers such as the ones shown allow for the rotational position of catheter 10 to be viewed by radiography or other imaging means. The marker configuration shown herein is important for both longitudinal and rotational positioning of catheter 10. When advanced into a bifurcation, it is critical for the user to know which way to orient the balloon such that the edges of the balloon are aligned with the vessel to be treated. As such, in some embodiments, as shown in FIG. 8A, catheter 10 includes multiple markers along shaft 12, indicating specific locations along balloon 20. In the embodiment shown in FIG. 8A, a first distal marker 34 is positioned at balloon distal end 22 aligned with distal long wall portion 27, a second distal marker 37 is aligned with distal short wall portion 29, a first proximal marker 36 is positioned at balloon proximal end 24 aligned with long wall portion 26, and a second proximal marker 35 is aligned with a short wall portion 28 of balloon 20.

In embodiments of the invention, only first proximal marker 36 is used at a proximal end of balloon 20, in which case, first proximal marker 36 approximates an angle of balloon proximal end 24. Thus, for example, first proximal marker 36 may have a tilted ring configuration, such as depicted in FIG. 8A. In some embodiments, first and second proximal markers 36 and 35 may also each include an eccentric element portion 77, such that the eccentric element portions 77 are on opposite sides of shaft 12 to indicate rotational positioning of long wall portion 26 and short wall portion 28. Similarly, first distal marker 34 may have a tilted ring configuration such as depicted in FIG. 8A, and in some embodiments may be the only distal marker used. First distal marker 34 as well as second distal marker 37 may also include eccentric element portions (not shown) to indicate rotational positioning of distal long wall portion 27 and distal short wall portion 29.

Alternatively, first proximal marker 36 and/or first distal marker 34 may have a triangular configuration as shown in cross-section in FIG. 8B. In FIG. 8B, this is shown for only first proximal marker 36 but it should be readily apparent that a similar design may be used for first distal marker 34. This triangular design may be accomplished, for example, by using a ring having a wide portion and a narrow portion, wherein the angle formed between the wide portion and the narrow portion approximates the angle of balloon proximal end 24 (shown in FIG. 1A, for example, by arrows 25). In some embodiments, when distal end of balloon 20 is symmetrical rather than oblique, as shown in FIG. 8B, first distal marker 34 may have a ring configuration, and may completely or partially surround shaft 12 at balloon distal end 22. In addition, at least two proximal markers may be suitably configured and arranged on the shaft or balloon eccentrically opposite to each other so that the visible elements of the markers are opposite to each other, thereby permitting control of rotational position of the catheter/balloon, as shown in FIG. 8A, for example.

In some embodiments, as shown in FIG. 8C, markers may be positioned on balloon 20 or incorporated within the material of balloon 20, either instead of or in addition to markers on shaft 12. For example, a tilted marker 39 may be positioned at balloon proximal end 24 when balloon 20 is in an unexpanded state. Similarly, additional markers may be positioned at balloon distal end 22.

Referring again to FIG. 5, in embodiments wherein an oblique stent is positioned on balloon 20, stent 40 may further include one or multiple distal stent markers 42 and at least a first proximal stent marker 44 and a second proximal stent marker 45. Stent 40 is shown having a stent distal end 43 and a stent proximal end 41. At stent proximal end 41, stent 40 has an oblique shape when expanded, such that a long wall portion 47 of oblique stent 40 extends past a short wall portion 49 of oblique stent 40 in a proximal direction such that stent proximal end 41 is substantially at an oblique angle to a plane which is perpendicular to longitudinal axis 30 when stent 40 is in an expanded state. The oblique angle is shown schematically in FIG. 5 by arrows 25.

In embodiments of the invention, first proximal stent marker 44 is positioned on a proximal end of long wall portion 47 of oblique stent 40, and second proximal marker 45 is positioned on a proximal end of short wall portion 49 of oblique stent 40. This configuration enables visualization even when stent 40 is in its unexpanded state, during introduction of catheter 10 into the vessel. This allows for proper alignment and positioning.

In order to enable delivery of a balloon catheter as in the invention, torque forces must be transferable to shaft distal end 14 from shaft proximal end 16. Typically, as described above with reference to FIG. 1A, for example, shaft 12 is comprised of a torqueable stiff segment 17 from shaft proximal end 16 to transition segment 53, which is an area or a point proximal to shaft distal end 14. Shaft distal end 14 is typically flexible so as to allow for balloon 20 to conform to the twists and turns of the vessel. Thus, if one were to try to rotate balloon 20 in order to align the shape with the ostium of the branch, balloon 20 would twist and would not be easily rotatable. As such, it would be advantageous to include a torque transmission mechanism 50 for transmitting torque of at least 180° and in at least one rotational direction from stiff segment 17 of shaft 12 to the more flexible shaft distal end 14, as will be described in greater detail hereinbelow.

Figure 9A:
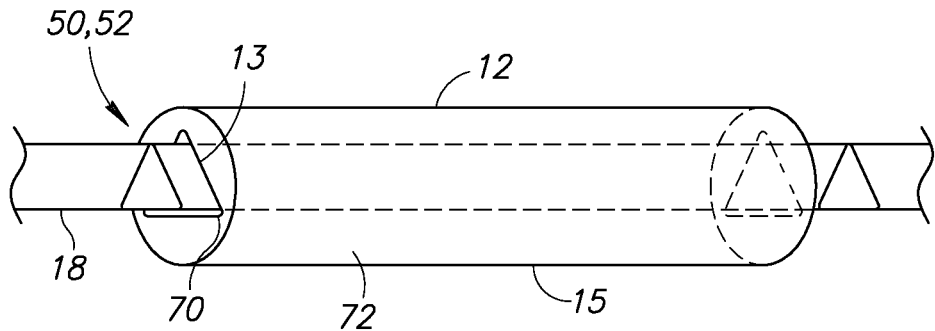
FIGS. 9A-9C are a perspective illustration and cross-sectional illustrations, respectively, of a torque transmission mechanism in accordance with one embodiment of the invention.
Figure 9B:
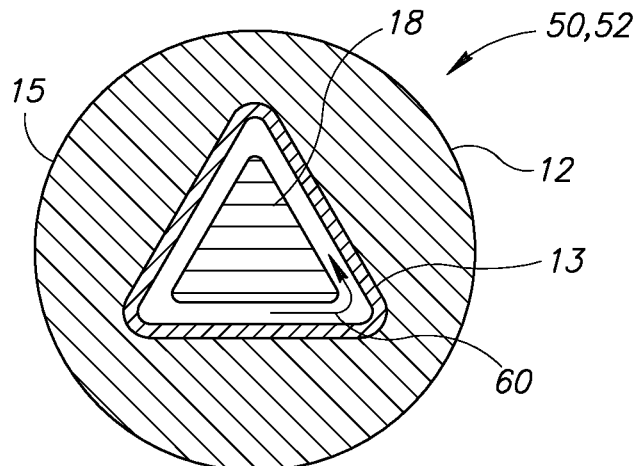
Figure 9C:
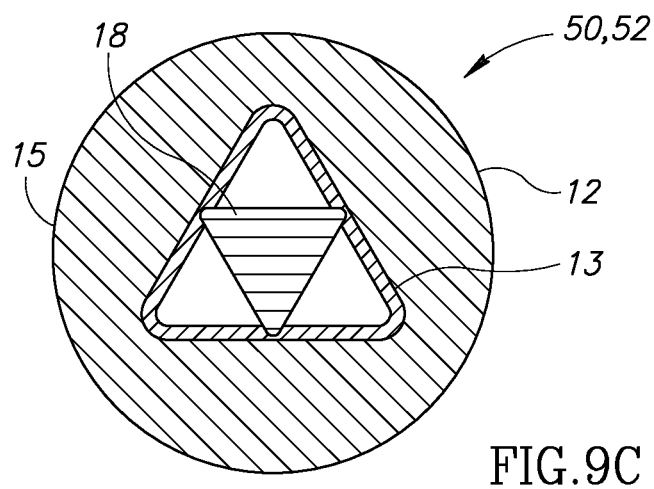

Reference is now made to FIGS. 9A-9C, which are a perspective illustration and two cross-sectional illustrations, respectively, of a torque transmission mechanism 50 in accordance with one embodiment, wherein torque transmission mechanism 50 is a key lock mechanism 52 between at least a portion of shaft 12 and guidewire 18. Key lock mechanism 52 is configured by shaping at least a portion of shaft 12 at or distal to transition segment 53, and/or shaping at least a portion of guidewire 18, such that friction is created between guidewire 18 and shaft 12 when shaft 12 and guidewire 18 are positioned relative to each other and are interlocked with one another. In one embodiment, as shown in FIGS. 9A-9C, at least a segment of an internal wall portion 13 of shaft 12 and at least a portion of guidewire 18 have a substantially triangular shape, for example. It should be readily apparent that other shapes may be used, such as ovoid, diamond, or any other suitable shape. An external wall portion 15 of shaft 12 may, but does not necessarily, have the same shape as internal wall portion 13, and may be round so that shaft 12 appears from the outside to have a substantially round diameter. Guidewire 18 may have a shaped portion 70, at a particular segment thereof or along its length. Shaft 12 may also have a shaped portion 72 at a particular segment thereof or along its length. Shaft 12 can initially be advanced over guidewire 18 longitudinally until the shaped portion 70 of guidewire 18 is positioned within the shaped portion 72 of shaft 12, as shown in cross-section in FIG. 9B. Guidewire 18 may thereby interlock with shaft 12 or may be rotated as shown by arrow 60, until the shapes of guidewire 18 and shaft 12 do not align, as shown in FIG. 9C. This then results in an interlocking of guidewire 18 and shaft 12 such that torque applied to a proximal end of the catheter 10 (i.e. stiff segment 17) and a proximal end of guidewire 18 will be better transmitted past the transition segment 53 and to the distal end of balloon catheter 10 than if torque were applied to a balloon catheter 10 without a torque transmission mechanism. In some embodiments, the shaped portion 72 of internal wall portion 13 may extend along the entire length of shaft 12. In other embodiments, the shaped portion 72 of internal wall portion is included only at a portion of shaft 12, such as at or near transition segment 53 or distal to transition segment 53 between stiff segment 17 and flexible segment 19. In yet additional embodiments, the shaped portion 72 of internal wall portion is included at or near the tip of balloon 20. In some embodiments, the shaped portion 70 of guidewire 18 extends along the entire length of guidewire 18. In other embodiments, the shaped portion 70 of guidewire 18 is included at a segment of guidewire 18, such as a distal segment of guidewire 18.

Figure 10:
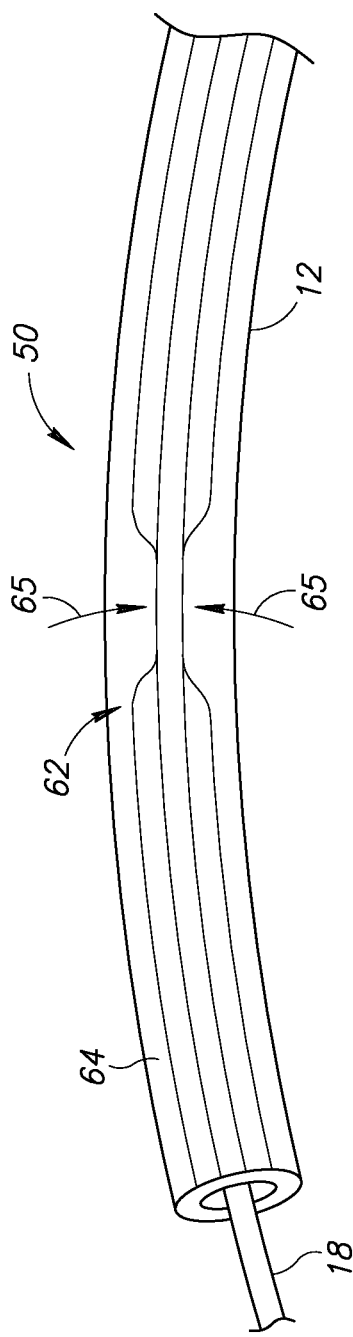
FIG. 10 is a perspective illustration of a torque transmission mechanism in accordance with another embodiment of the invention.

Reference is now made to FIG. 10, which is an illustration of key lock mechanism 50 in accordance with additional embodiments. In this embodiment, locking may occur by application of an external force upon shaft 12, forcing shaft 12 into a shape which locks guidewire 18 in place. For example, shaft 12 may include a locally compressible section 62 surrounded by an inflation lumen 64. Inflation fluid or other medium may be introduced into inflation lumen 64, which causes compressible section 62 to be compressed via inflation pressure, as shown by arrows 65. In some embodiments, inflation lumen 64 also serves as a balloon inflation lumen for inflating balloon 20. Compressible section 62 may be designed such that a lower inflation pressure than that needed for inflating balloon 20 causes compressible section 62 to be compressed. Once compressible section 62 is compressed, guidewire 18 will not rotate freely within shaft 12 due to the compression. In some embodiments, compressible section 62 of internal wall portion 13 may extend along the entire length of shaft 12. In other embodiments, compressible section 62 of internal wall portion is included only at or near transition segment 53 between stiff segment 17 and flexible segment 19. In yet additional embodiments, compressible section 62 of internal wall portion is included at flexible segment 19 or at or near the tip of balloon 20. In another embodiment (not shown) a fixed or movable sheath surrounding the shaft and extending at least from the transition segment to or near the balloon is used to reinforce and transmit torque from stiff segment 17 to the balloon.

Figure 11:
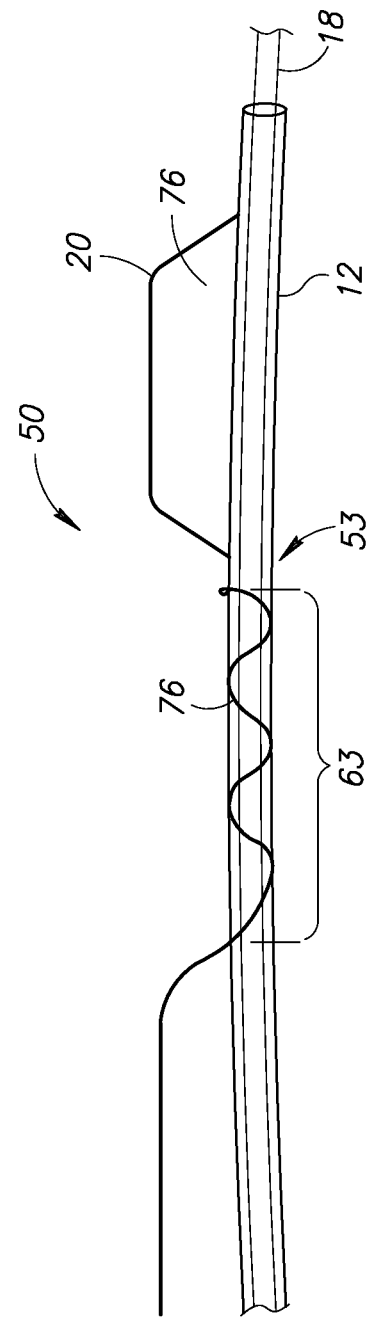
FIG. 11 is a perspective illustration of a torque transmission mechanism in accordance with yet another embodiment of the invention.

Reference is now made to FIG. 11, which is an illustration of torque transmission mechanism 50, in accordance with yet additional embodiments. In this embodiment, improved torque transmission may occur by application of an external force upon shaft 12. For example, shaft 12 may include a torque transmission section 63 surrounded by a spiral pull wire 76. Pulling proximally on spiral pull wire 76 causes torque transmission section 63 to be rotated via mechanical pull force. In some embodiments, the spiral pull wire 76 is included only at or distal to transition segment 53 between stiff segment 17 and flexible segment 19. In yet additional embodiments, the spiral pull wire 76 is included at flexible segment 19 or at or near the distal end of balloon 20.

Figure 12A:
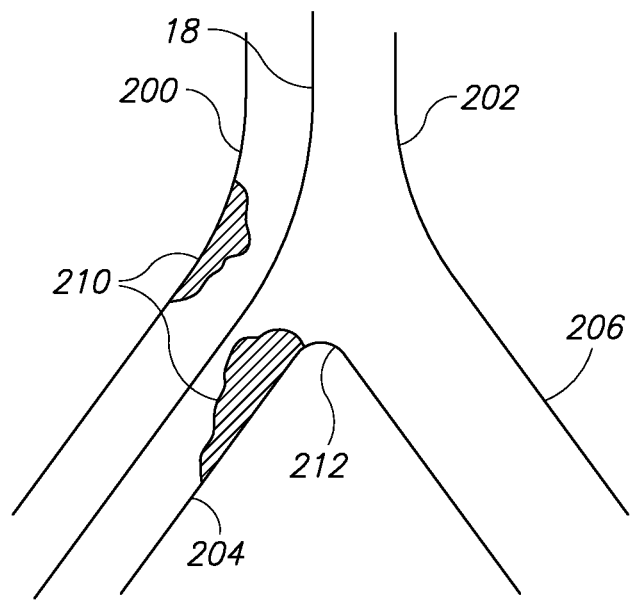
FIGS. 12A-12E are illustrations of a method of providing a balloon at a bifurcation, in accordance with embodiments of the invention.
Figure 12B:
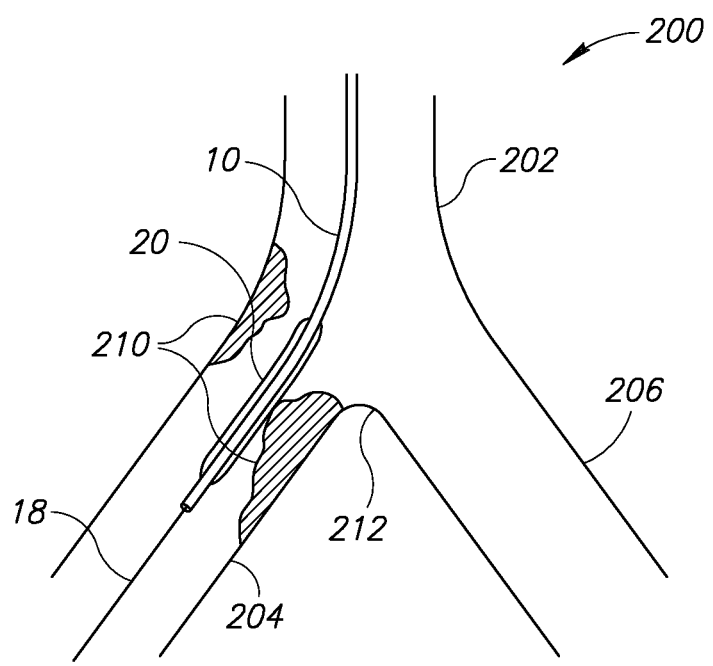
Figure 12C:
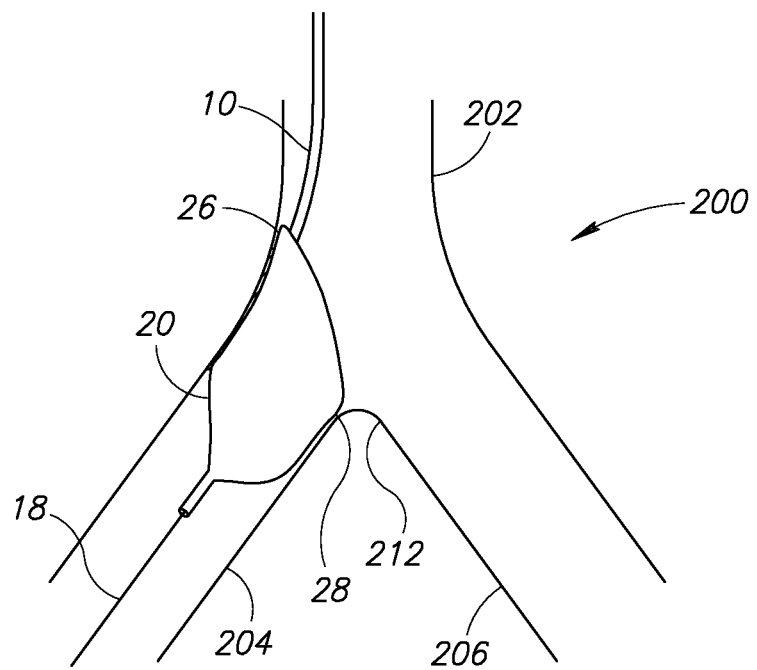
Figure 12D:
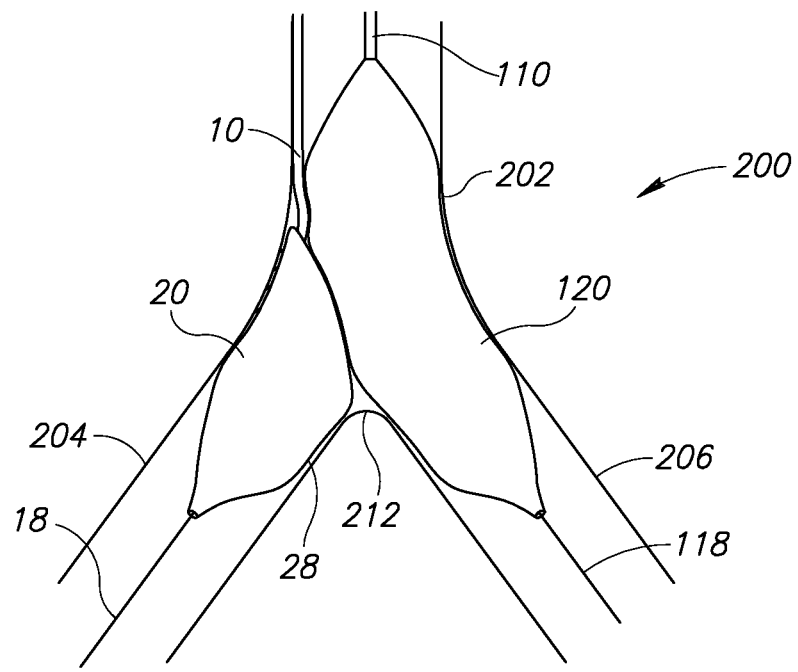
Figure 12E:
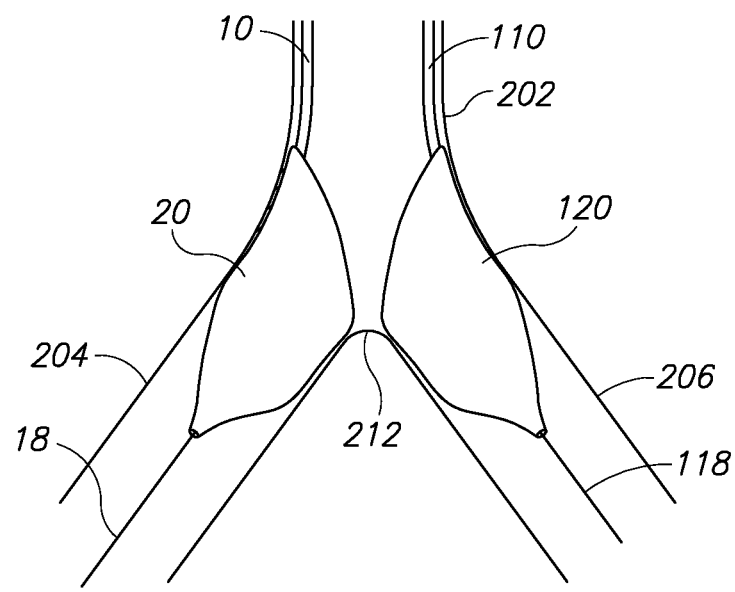

Reference is now made to FIGS. 12A-12E, which are illustrations of a method of providing a balloon at a bifurcation, in accordance with embodiments of the invention. First, as shown in FIG. 12A, guidewire 18 is introduced into a vessel 200. Vessel 200 is a bifurcated vessel, and may have a Y-configuration for example. Vessel 200 has a main vessel 202, a first branch vessel 204, and a second branch vessel 206. A lesion 210 is located at a junction 212 between first branch vessel 204 and second branch vessel 206. Guidewire 18 may be introduced through main vessel 202 and into first branch vessel 204, for example. As shown in FIG. 12B, catheter 10 with balloon 20 positioned thereon is then advanced over guidewire 18 into first branch vessel 204. In some embodiments, catheter 10 has a fixed wire at its distal end and is advanced without a separate guidewire 18. As shown in FIG. 12C, balloon 20 is expanded and assumes an oblique shape. In order for balloon 20 to be positioned correctly within vessel 200, catheter 10 must be rotatable or torquable, such that long wall portion 26 of balloon 20 remains at the most proximal branchpoint of first branch vessel 204 and does not extend substantially into main vessel 202, while short wall portion does not extend past junction 212, i.e., the carina. Markers on catheter 10 can help guide location of balloon 20 within vessels 200— including vessels 202, 204 and 206. As shown in FIG. 12D, a second catheter 110 may be introduced through main vessel 202 and into second branch vessel 206 over a second guidewire 118. A second balloon 120 is inflated, and may contact the first balloon 20, such that lesion 210 can be treated without plaque shift. This can be done wherein second balloon 120 is a conventional balloon, as shown in FIG. 12D. Alternatively, second balloon 120 may be another oblique balloon, as shown in FIG. 12E.

Figure 13A:
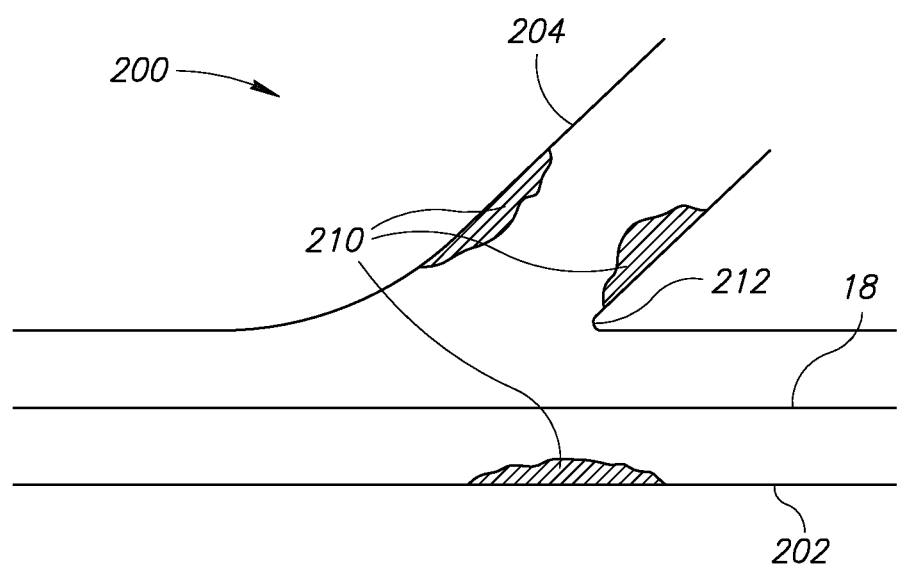
FIGS. 13A-13E are illustrations of a method of providing a balloon and a stent at a bifurcation, in accordance with embodiments of the invention.
Figure 13B:
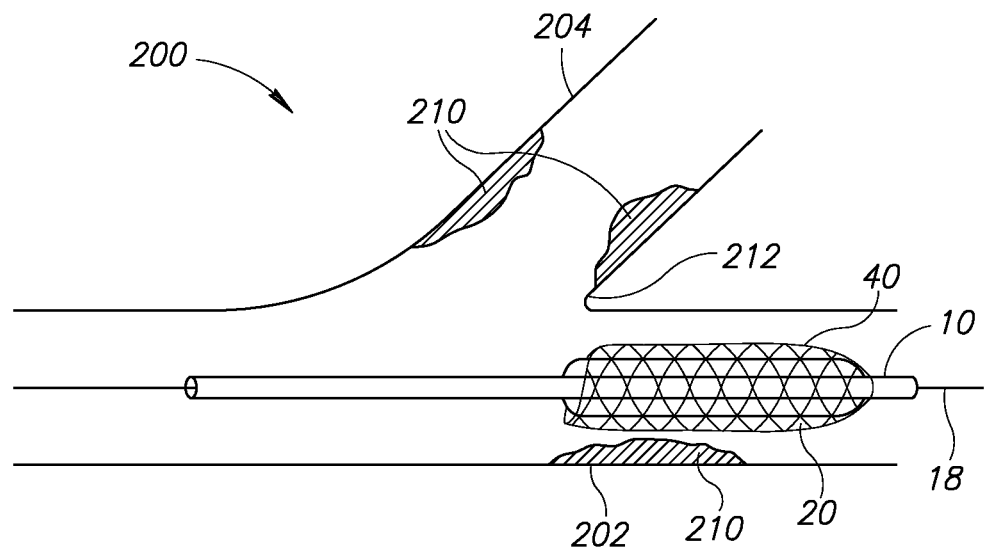
Figure 13C:
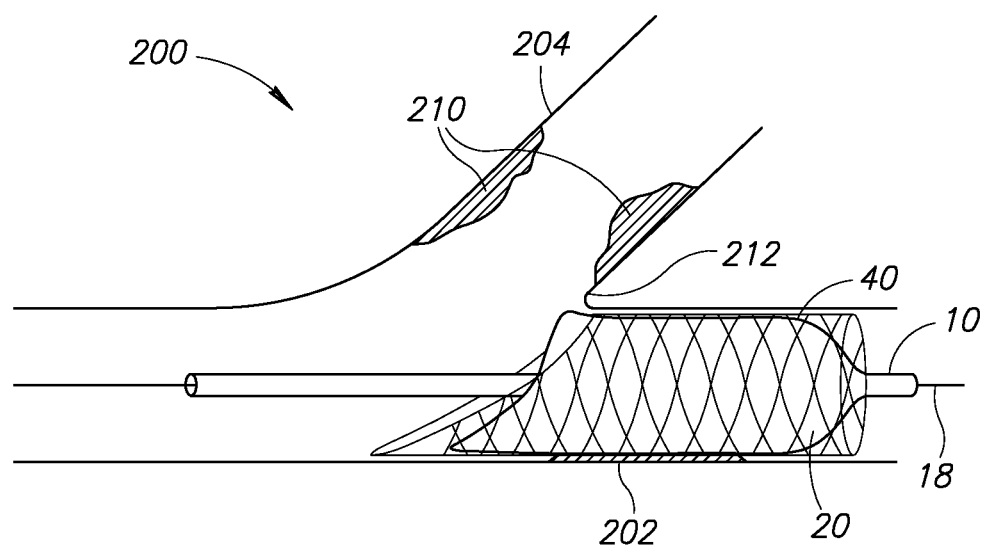
Figure 13D:
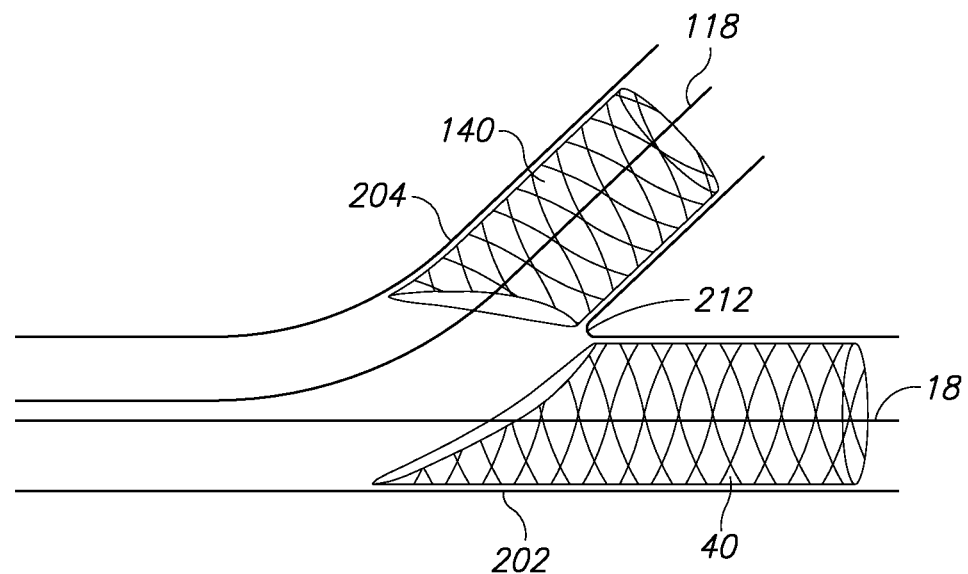
Figure 13E:
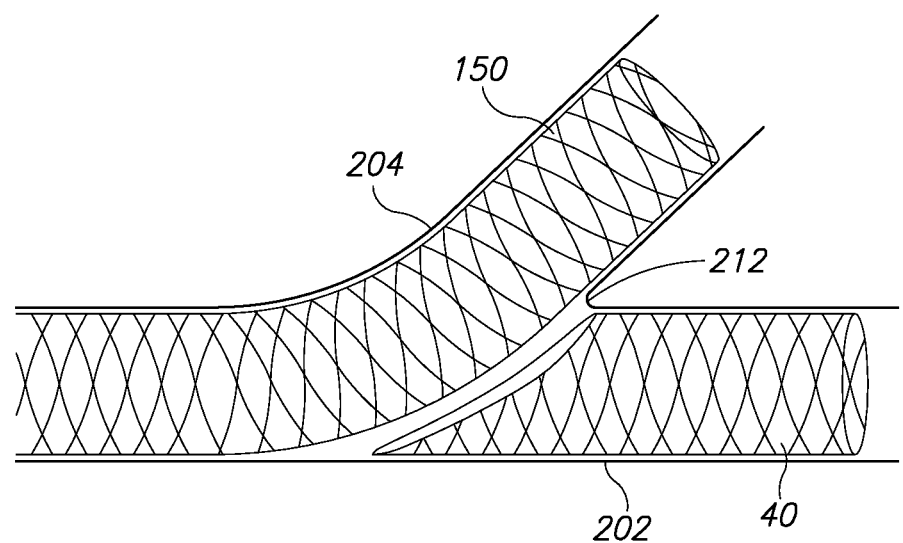

Reference is now made to FIGS. 13A-13E, which are illustrations of a method of providing an oblique stent at a bifurcation, in accordance with embodiments of the invention. As shown in FIG. 13A, a guidewire 18 is introduced into a vessel 200 having a main branch 202 and a side branch 204, with a lesion 210 at a bifurcation point 212 of main branch 202 and side branch 204. As shown in FIG. 13B, catheter 10 having balloon 20 and an oblique stent 40 positioned thereon, is introduced into main branch 202 past bifurcation point 212, with the short side of the proximal end of balloon 20 and the short side of the proximal oblique end of stent 40 positioned at the bifurcation point 212 (i.e. the carina). As shown in FIG. 13C, oblique balloon 20 is expanded, thus deploying oblique stent 40 within vessel 202 without substantial protrusion of stent 40 into vessel 200. As shown in FIG. 13D, a second catheter having a balloon and a second oblique stent 140 positioned thereon is introduced into side branch 204. The second catheter with balloon may be advanced over a second guidewire 118. The second balloon is expanded, thus deploying the second oblique stent 140 within vessel 204. Subsequently, balloon or balloons 20 may be deflated and catheter or catheters 10 removed from vessel 200, 202 and 204, leaving stent or stents 40, 140 in place. Alternatively, as shown in FIG. 13E, after stent 40 is deployed in either main branch 202 or side branch 204, a conventional catheter and conventional stent 150 may be positioned in the other vessel, bridging the area of bifurcation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. For example, balloon 20 can be any type of balloon and appropriate material, including, but not limited to, scoring balloons (i.e. balloons in cages), all types of drug eluting balloons, coronary artery and peripheral artery balloons, brain artery balloons or balloons for other body luminal organs, balloons for carrying any type of coronary or peripheral artery stents or stents for other luminal organs including bare metal stents, drug eluting stents, biodegradable or bioabsorbable scaffolds, stent-grafts, covered stents or any other stent or luminal scaffold type of implant including self-expandable or balloon-expandable or any other type. The terms stent and scaffold in this invention are used to embrace all above mentioned variations, modifications and types of stents, scaffolds and scaffolding devices and all materials used for those devices alone or in combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the invention.

What is claimed is:

1. A balloon catheter for treatment of a vessel at a bifurcation, the balloon catheter comprising:
   a shaft having a shaft distal end and a shaft proximal end along a longitudinal axis; and
   a balloon positioned on said shaft, said balloon having a balloon distal end and a balloon proximal end along said longitudinal axis, wherein said balloon proximal end has a long wall portion and a short wall portion opposite said long wall portion wherein said long wall portion extends past said short wall portion in a proximal direction along said longitudinal axis forming a beveled tip, such that said balloon proximal end is substantially at an oblique angle to a plane which is perpendicular to said longitudinal axis when said balloon is in an expanded state, wherein when said balloon is in an expanded state said shaft is eccentric to a central axis of said balloon at said balloon proximal end and said shaft is positioned substantially at the central axis of said balloon at said balloon distal end, wherein said shaft further comprises a first proximal marker on said shaft at a proximal end of said long wall portion and a second proximal marker on said shaft at a proximal end of said short wall portion, wherein said first proximal marker and said second proximal marker each have an eccentric element portion on opposite sides of the shaft.

2. The balloon catheter of claim 1, wherein said shaft is at least partially a guidewire shaft configured to hold a guidewire therein.

3. The balloon catheter of claim 1, wherein said shaft is positioned through said balloon and adjacent to said long wall portion at said balloon proximal end.

4. The balloon catheter of claim 1, wherein said shaft is angled within said body of said balloon.

5. The balloon catheter of claim 1, wherein said first proximal marker has a triangular shape having an angle approximating said oblique angle.

6. The balloon catheter of claim 1, wherein said first proximal marker has a tilted ring configuration approximating said oblique angle.

7. The balloon catheter of claim 1, wherein at least a portion of said first proximal marker is positioned on an opposite side of said shaft from at least a portion of said second proximal marker.

8. The balloon catheter of claim 1, further comprising an oblique stent or scaffold positioned on said balloon, wherein a proximal end of said oblique stent or scaffold is configured at an oblique angle to said plane which is perpendicular to said longitudinal axis.

9. The balloon catheter of claim 1, wherein the balloon has a cone shape and wherein a diameter of said balloon proximal end is greater than a diameter of said balloon distal end when said balloon is in an expanded state.

10. The balloon catheter of claim 1, further comprising a torque transmission mechanism, wherein said torque transmission mechanism is a key lock mechanism for interlocking of a guidewire and said shaft.

11. The balloon catheter of claim 1, wherein a proximal portion of said beveled tip is connected to said shaft.

12. A balloon catheter, the balloon catheter comprising:
    a shaft having a shaft distal end and a shaft proximal end along a longitudinal axis; and
    a balloon positioned on said shaft, said balloon having a balloon first end and a balloon second end along said longitudinal axis, wherein at said balloon first end, said shaft is positioned through said balloon and adjacent to an edge of said balloon and wherein at said second balloon end, said shaft is positioned substantially at the central axis of said balloon, such that at said balloon first end, said shaft is eccentric to a central axis of said balloon and at said balloon second end said shaft is substantially concentric to the central axis of said balloon when said balloon is in an expanded state, wherein said shaft further comprises a first proximal marker on said shaft at a proximal end of said long wall portion and a second proximal marker on said shaft at a proximal end of said short wall portion, wherein said first proximal marker and said second proximal marker each have an eccentric element portion on opposite sides of the shaft.

13. The balloon catheter of claim 12, wherein said balloon proximal end has a long wall portion and a short wall portion opposite said long wall portion wherein said long wall portion extends past said short wall portion in a proximal direction along said longitudinal axis forming a beveled tip, such that said balloon proximal end is substantially at an oblique angle to a plane which is perpendicular to said longitudinal axis when said balloon is in an expanded state.

14. The balloon catheter of claim 12, further comprising a torque transmission mechanism, wherein said torque transmission mechanism is a key lock mechanism.

15. The balloon catheter of claim 12, wherein said shaft is positioned through said balloon and adjacent to said long wall portion at said balloon proximal end.

16. The balloon catheter of claim 12, wherein said shaft is angled within said body of said balloon.

17. The balloon catheter of claim 12, wherein said first proximal marker has a triangular shape having an angle approximating said oblique angle.

18. The balloon catheter of claim 12, wherein said first proximal marker has a tilted ring configuration approximating said oblique angle.

19. The balloon catheter of claim 12, further comprising an oblique stent or scaffold positioned on said balloon, wherein a proximal end of said oblique stent or scaffold is configured at an oblique angle to said plane which is perpendicular to said longitudinal axis.

20. The balloon catheter of claim 12, wherein the balloon has a cone shape and wherein a diameter of said balloon proximal end is greater than a diameter of said balloon distal end when said balloon is in an expanded state.

* * * * *